(12) United States Patent
Valenti et al.

(10) Patent No.: US 9,282,983 B2
(45) Date of Patent: Mar. 15, 2016

(54) DEVICE FOR GUIDING PIERCING TOOLS FOR PLACING A GLENOID IMPLANT

(71) Applicants: FOURNITURES HOSPITALIERES INDUSTRIE, Quimper (FR); Philippe Valenti, Paris (FR); F.H. INC., Chicago, IL (US)

(72) Inventors: Philippe Valenti, Paris (FR); Alain Aaron, Saint Witz (FR)

(73) Assignees: FOURNITURES HOSPITALIERES INDUSTRIE (FR); Philippe Valenti (FR); F.H. INC., Chicago, IL (US)

( * ) Notice: Subject to any disclaimer, the term of this patent is extended or adjusted under 35 U.S.C. 154(b) by 223 days.

(21) Appl. No.: 13/894,809

(22) Filed: May 15, 2013

(65) Prior Publication Data

US 2014/0343556 A1  Nov. 20, 2014

(51) Int. Cl.
*A61B 17/17* (2006.01)

(52) U.S. Cl.
CPC ..... *A61B 17/1739* (2013.01); *A61B 2017/1778* (2013.01)

(58) Field of Classification Search
CPC .............................. A61B 17/70; A61B 17/1739
USPC ............... 606/80, 86 R, 87–89, 96, 102, 104; 623/19.11–19.14
See application file for complete search history.

(56) References Cited

U.S. PATENT DOCUMENTS

| | | | | |
|---|---|---|---|---|
| 5,312,412 A | * | 5/1994 | Whipple | A61B 17/1739 606/105 |
| 5,437,677 A | * | 8/1995 | Shearer | A61B 17/1739 606/80 |
| 5,688,284 A | * | 11/1997 | Chervitz | A61B 17/1764 606/102 |
| 8,702,717 B2 | * | 4/2014 | Rauscher | A61B 17/1739 606/104 |
| 2004/0230197 A1 | * | 11/2004 | Tornier | A61B 17/1739 606/87 |
| 2008/0015608 A1 | * | 1/2008 | Colquhoun | A61B 17/1675 606/87 |
| 2010/0324563 A1 | * | 12/2010 | Green, II | A61F 2/4657 606/89 |
| 2012/0123417 A1 | * | 5/2012 | Smith | 606/80 |

* cited by examiner

*Primary Examiner* — Christopher Beccia
(74) *Attorney, Agent, or Firm* — Cantor Colburn LLP

(57) ABSTRACT

A guide device having a guide body including a bearing surface designed to bear in a glenoidal cavity of a scapula that has been prepared beforehand, the guide body including at least one through orifice emerging in the bearing surface, a reference member mounted on the guide body and including a bearing portion designed to bear on the anterior cortex of the scapula, and adjustment means arranged to adjust the position of the reference member with respect to the guide body so as to adjust the distance between the bearing portion and an axis of the through orifice.

17 Claims, 4 Drawing Sheets

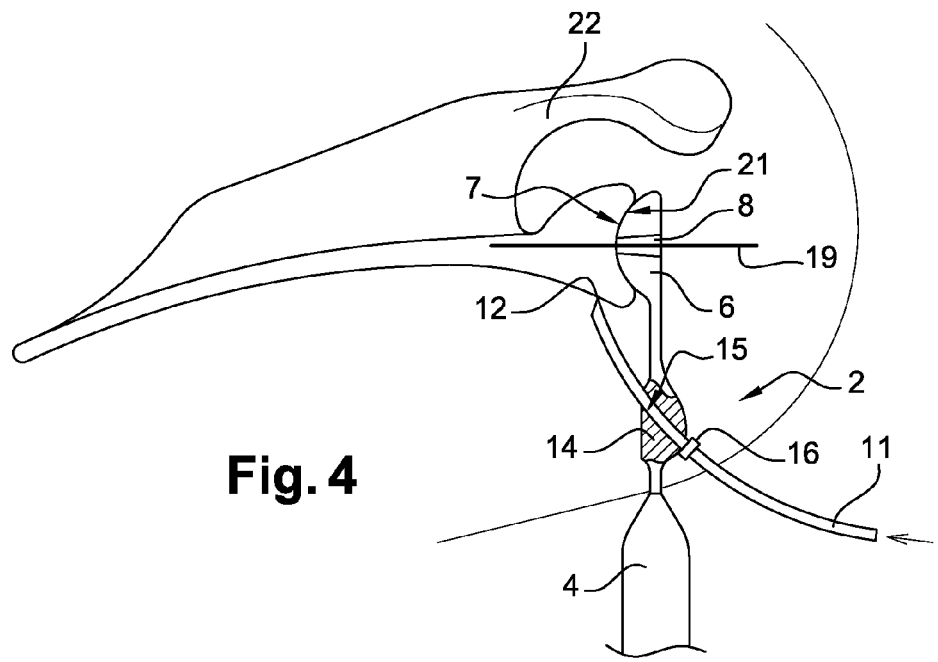
Fig. 4
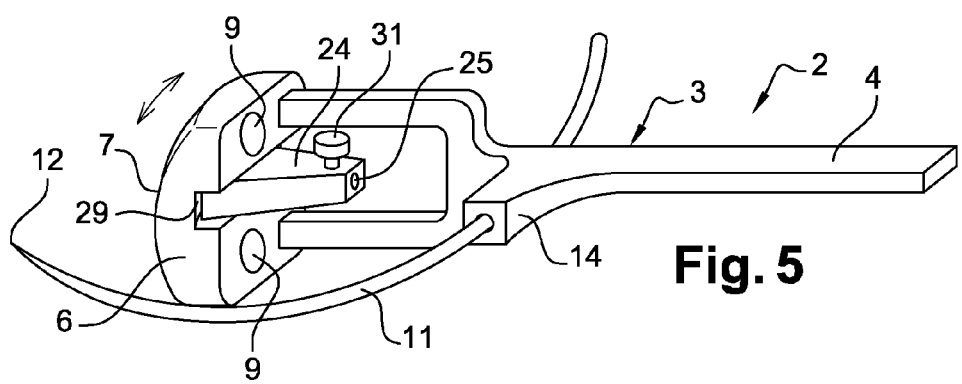
Fig. 5
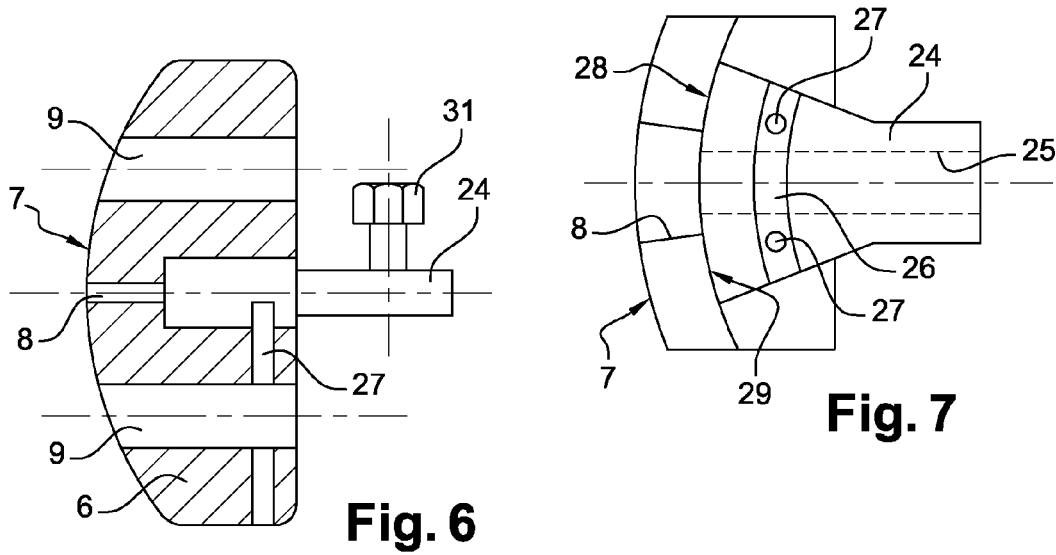
Fig. 6
Fig. 7

DEVICE FOR GUIDING PIERCING TOOLS FOR PLACING A GLENOID IMPLANT

TECHNICAL FIELD

The present invention relates to a device for guiding piercing tools for placing a glenoid implant.

BACKGROUND

The deterioration of the humeral head and the glenoid by primary or secondary osteoarthritis causes a loss of articular congruence, which is a source of pain and limits the mobility of the shoulder.

One solution to offset this joint deterioration consists of implementing a complete shoulder prosthesis including a humeral head designed to be engaged in the medullary channel of the humerus, and a glenoid implant designed to be implanted in the glenoidal cavity of the scapula. Such a complete shoulder prosthesis may be anatomical or said to be reversed when the convexity of the glenoid is transferred to the location of the humeral head.

The fastening of the glenoid implant in a glenoidal cavity requires producing one or more bone drillings in the latter designed to house the fastening element(s) provided on the glenoid implant, such as a fin or fastening studs.

Because of the anatomy of the glenoid and the scapula and the low bone capital of the bony vault of the glenoid, the production of such bone drillings must be done precisely so as to limit the risks of perforation of the bony vault of the glenoid and therefore the risks of subsequent conflicts between the fastening element(s) of the glenoid implant and the anterior or posterior cortex of the scapula. Such conflicts may harm the stability of the final implant and impose removal of the shoulder prosthesis. Furthermore, protrusion of the fastening elements outside the bone would cause friction of the latter on the muscles or nerves (suprascapular), which may cause pain for the patient.

In order to limit the risks of such conflicts, it is known to use a device for guiding piercing tools as described in document U.S. Pat. No. 5,437,677.

The guide device described in document U.S. Pat. No. 5,437,677 comprises:
 a support plate provided with an indexing member including a bearing portion designed to bear on the anterior cortex of the scapula,
 a guide body comprising a bearing surface designed to bear in a previously prepared glenoidal cavity of the scapula, and a through orifice emerging in the bearing surface, the guide body being slidingly mounted on the support plate in a movement direction parallel to the axis of the through orifice, and
 means for immobilizing the guide body with respect to the support plate.

In order to prepare the glenoidal cavity for the placement of the glenoid implant, the surgeon positions the bearing portion of the reference member against the anterior cortex of the scapula, then moves the guide body toward the glenoidal cavity until the bearing surface of the guide body bears against the glenoidal cavity, and then immobilizes the guide body with respect to the support plate using immobilizing means. Lastly, the surgeon inserts a piercing tool through the through orifice of the guide body and produces a bone drilling in the glenoidal cavity.

It should be noted that the distance separating the axis of the through orifice and the bearing portion is defined such that, when the bearing portion of the reference member is in contact with the anterior cortex of the scapula, the axis of the through orifice extends in the central part of the glenoid neck.

Such a guiding device consequently makes it possible to greatly limit the risks of perforation of the bony vault of the glenoid, and therefore the risks of removal the shoulder prosthesis by pulling free of the glenoid.

However, such a guide device may be unsuitable for implanting glenoid implants in patients with a particular anatomy or significant deteriorations of the glenoid. In fact, in these particular cases, the definition of the distance separating the axis of the through orifice and the bearing portion may be such that the bone drilling done will extend in an area of the glenoid having poor bone quality or will emerge in the anterior cortex of the scapula.

BRIEF SUMMARY

The present invention aims to resolve these drawbacks.

The technical problem at the base of the invention therefore consists of providing a device for guiding piercing tools for placing a glenoid implant that has a simple, compact and cost-effective structure, and that makes it possible to ensure optimal implantation of the glenoid implant irrespective of the anatomy and pathology of the patient to be treated.

To that end, the present invention relates to a guide device for guiding piercing tools for placing a glenoid implant, comprising:
 a guide body comprising a bearing surface designed to bear in a glenoidal cavity of a scapula that has been prepared beforehand, for example by burring, the guide body comprising at least one through orifice emerging in the bearing surface,
 a reference member mounted on the guide body and including a bearing portion designed to bear on the anterior cortex of the scapula, and
 adjustment means arranged to adjust the position of the reference member with respect to the guide body so as to adjust the distance between the bearing portion and an axis of the through orifice.

The axis of the through orifice in particular refers to the axis of symmetry, the geometric axis, or a general extension axis of the through orifice.

The configuration of the adjustment means allows the surgeon to modify the distance between the bearing portion of the reference member and the axis of the through orifice so as to account for the anatomy of the patient to be treated, and more particularly to adjust that distance to an optimal value determined using imaging of the patient's shoulder.

The guide device according to the invention thus makes it possible to greatly limit the risks of removal of a complete shoulder prosthesis, irrespective of the anatomy and pathology of the patient to be treated.

According to one embodiment of the invention, the through orifice is designed for the passage of a support pin implanted in the glenoidal cavity.

Advantageously, the guide body comprises an mounting portion on which the reference member is movably mounted.

According to one embodiment of the invention, the reference member is slidingly mounted on the mounting portion.

According to one embodiment of the invention, the adjustment means include a stop member movably assembled on the reference member, the stop member being arranged to cooperate with the mounting portion so as to limit the travel of the reference member with respect to said mounting portion in at least one movement direction.

According to one embodiment of the invention, the adjustment means include immobilizing means for immobilizing the stop member with respect to the reference member.

According to one embodiment of the invention, the adjustment means include a thread formed on the reference member and arranged to cooperate with a tapped assembly orifice formed on the mounting portion.

According to one embodiment of the invention, the adjustment means comprise immobilizing means for immobilizing the reference member with respect to the guide body.

According to one embodiment of the invention, the adjustment means include graduations provided on the reference member and representing the distance between the bearing portion and the axis of the through orifice. For example, the stop member or the mounting portion is configured to cooperate with the graduations provided on the reference member so as to adjust the distance between the bearing portion and the axis of the through orifice.

Advantageously, the passage channel has a passage cross-section smaller than the passage cross-section of the through orifice.

According to one embodiment of the invention, the through orifice comprises a travel portion arranged so as to allow an angular travel of the guide device along a first travel portion when a support pin implanted in the glenoidal cavity is inserted into the through orifice. The travel portion is for example configured so as to allow an angular travel of the guide device of approximately 10° on either side of a support pin inserted through orifice.

According to one embodiment of the invention, the width of the travel portion decreases toward the bearing surface.

According to one embodiment of the invention, the travel portion is oblong.

Advantageously, the height of the travel portion is substantially constant and substantially corresponds to the diameter of the support pin designed to be inserted into the through orifice.

Preferably, the through orifice is configured such that the width of the through orifice at the end thereof emerging in the bearing surface substantially corresponds to the diameter of the support pin designed to be introduced into the through orifice.

According to one embodiment of the invention, the guide device comprises a guide member including a passage channel arranged to emerge across from the through orifice and designed for the passage of the support pin, the guide member being mounted rotatably with respect to the guide body around an axis of rotation.

According to one embodiment of the invention, the guide member comprises a groove in the shape of an arc of circle with an axis substantially combined with the axis of rotation, and the guide device comprises at least two studs assembled on the guide body and arranged to cooperate with the arc of circle-shaped groove.

According to one embodiment of the invention, the guide member comprises a first guide surface formed by a cylindrical surface portion with an axis substantially combined with the axis of rotation and in which the passage channel emerges, and the guide body comprises a second guide surface complementary to the first guide surface and in which the through orifice emerges.

According to one embodiment of the invention, the guide member comprises fastening means arranged to fasten the guide member on a support pin inserted into the through orifice and extending in the passage channel.

According to one embodiment of the invention, the bearing surface is formed by a convex spherical surface portion.

These arrangements make it possible, when the glenoidal cavity has been prepared beforehand, for example by burring, so as to have a complementary concave spherical surface portion, to limit the movements of the guide device with respect to the glenoid to rotational movements centered on the shared center of the concave and convex surface portions. In this way, the guide device according to the invention ensures correct positioning of the piercings of the fastening elements by rotating the guide device in a substantially horizontal plane passing through the center of the concave spherical surface portion formed on the glenoidal cavity. Advantageously, the burring axis of the glenoidal cavity is embodied by a support pin previously inserted into the glenoid.

Advantageously, the center of the convex spherical surface portion is situated on the axis of the through orifice.

Advantageously, the center of the convex spherical surface portion is situated on the axis of rotation.

According to one embodiment of the invention, the guide body further comprises at least two through bores emerging in the bearing surface and each designed for the passage of a piercing tool.

Advantageously, the through bores are formed on either side of the through orifice, and preferably extend on either side of the extension plane of the travel portion of the through orifice.

According to one embodiment of the invention, the reference member is pivotably mounted on the mounting portion around the pivot axis, and the adjustment means include an actuating handle secured to the reference member.

Advantageously, the pivot axis extends substantially perpendicular to the extension plane of the travel portion of the through orifice.

According to one embodiment of the invention, the reference member is curved. The reference member may for example have a curve radius comprised between 60 and 100 mm, and advantageously a polygonal cross-section.

According to one embodiment of the invention, the mounting portion comprises a through assembly orifice through which the reference member extends.

According to one embodiment of the invention, the insertion point of the reference member into the assembly orifice is situated at a distance from the axis of the through orifice comprised between 60 and 100 mm, and for example approximately 80 mm.

According to one embodiment of the invention, the adjustment means are further arranged to adjust the position of the reference member with respect to the guide body so as to adjust the distance between the bearing portion and the center of the spherical surface portion parallel to the axis of the through orifice.

According to one embodiment of the invention, the guide device comprises a gripping sleeve secured to the guide body. The gripping sleeve may for example extend transversely, and in particular perpendicular, or parallel to the axis of the through orifice.

According to one embodiment of the invention, the guide device is made from a material withstanding autoclave sterilization.

BRIEF DESCRIPTION OF THE DRAWINGS

In any case, the invention will be well understood using the following description in reference to the appended diagrammatic drawing showing, as non-limiting examples, several embodiments of said guide device.

FIG. 4 is a cross-sectional view of the guide device of FIG. 1 under usage conditions.

FIG. 5 is a perspective view of a device for guiding piercing tools according to a second embodiment of the invention.

FIG. 6 is a transverse cross-sectional view of the guide device of FIG. 5.

FIG. 7 is a partial longitudinal cross-sectional view of the guide device of FIG. 5.

DETAILED DESCRIPTION

Figure 1:
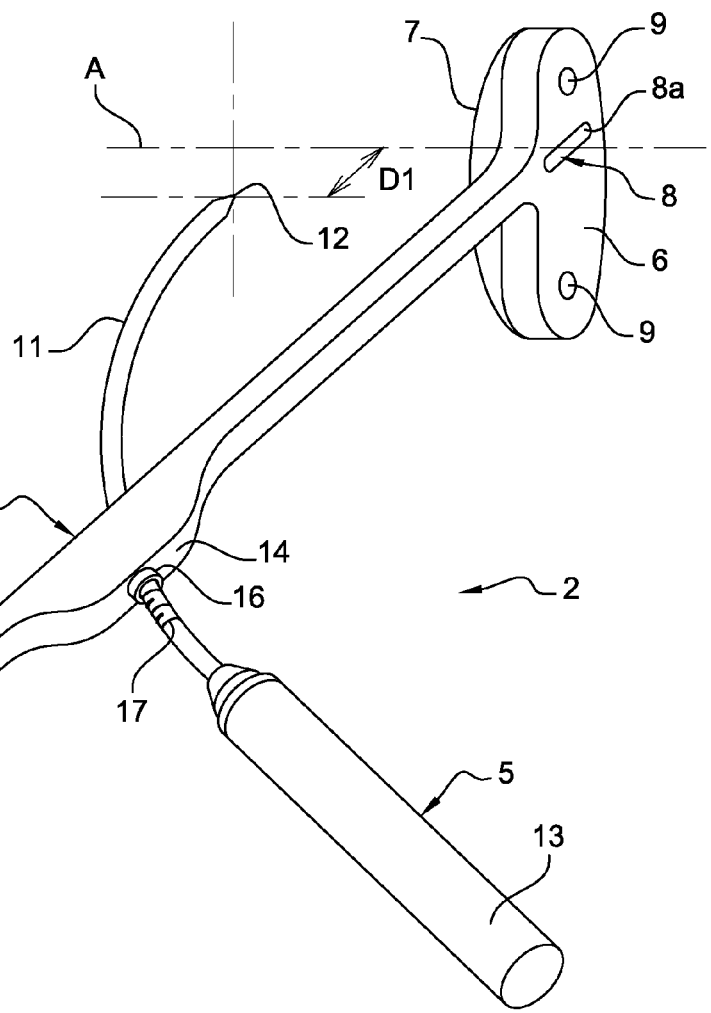
FIG. 1 is a perspective view of a device for guiding piercing tools according to a first embodiment of the invention.

FIGS. 1 to 4 show a guide device 2 for piercing tools for placing a glenoid implant for an anatomical or reverse shoulder prosthesis.

The guide device 2 comprises a guide body 3, a gripping sleeve 4 secured to the guide body 3 and a reference member 5 mounted on the guide body 3.

The guide body 3 more particularly comprises a bearing portion 6 provided with a bearing surface 7 designed to bear in a previously prepared glenoidal cavity of the scapula. The bearing surface 7 is advantageously formed by a convex spherical surface portion whereof the center is designed to be combined with the center of a concave spherical surface portion previously formed in the glenoidal cavity.

The bearing portion 6 further comprises a through orifice 8 emerging in the bearing surface 7 and designed for the passage of a support pin implanted in the glenoidal cavity, and two through bores 9 also emerging in the bearing surface 7 and each designed for the passage of the piercing tool to produce one or more holes in the glenoid designed to receive the fin or the fastening studs of the glenoid implant.

Figure 2:
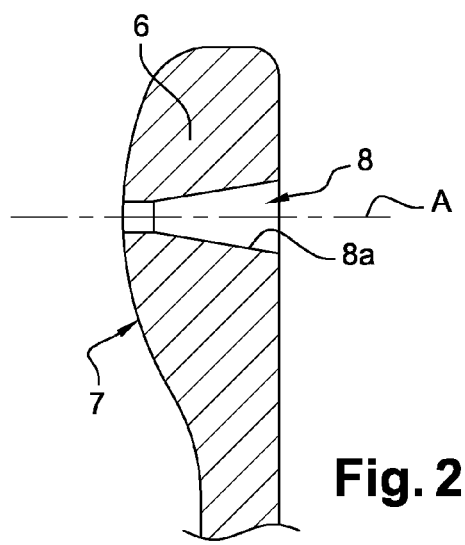
FIG. 2 is a partial longitudinal cross-sectional view of the guide device of FIG. 1.
Figure 3:
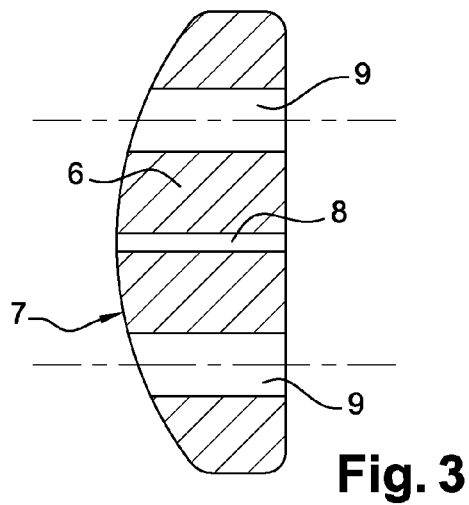
FIG. 3 is a transverse cross-sectional view of the guide device of FIG. 1.

As shown more particularly in FIGS. 1 and 2, the through orifice 8 comprises an oblong travel portion 8a whereof the width decreases toward the bearing surface 7 and the height of which is substantially constant. Advantageously, the height of the travel portion 8a and the width of the through orifice 8 at the end thereof emerging in the bearing surface 7 are substantially equal to the diameter of the support pin designed to be inserted into the through orifice 8. Preferably, the through bores 9 are formed on either side of the through orifice 8, and more particularly on either side of the extension plane of the travel portion 8a.

The travel portion 8a is advantageously configured so as to authorize an angular travel of the guide device 2 in a travel plane parallel to the extension plane of the travel portion 8a when a support pin implanted in the glenoidal cavity is inserted into the through orifice 8. The travel portion 8a is for example configured so as to allow an angular travel of the guide device 2 of approximately 10° on either side of said support pin inserted into the through orifice 8.

The reference member 5 includes a reference pin 11 provided with a bearing portion 12, preferably pointed, designed to bear on the outer anterior cortex of the scapula. The reference pin 11 may for example have a polygonal cross-section.

The reference member 5 may optionally further comprise a gripping sleeve 13 secured to the reference pin 11.

According to the embodiment shown in FIGS. 1 to 4, the reference pin 11 is curved, and has a curve radius comprised between 60 and 100 mm.

As shown in FIG. 4, the guide body 3 comprises an mounting portion 14 provided with a through assembly orifice 15 in which the reference pin 11 is slidingly mounted. The insertion point of the reference pin 11 into the assembly orifice 15 is advantageously situated at a distance from the axis A of the through orifice 8 comprised between 60 and 100 mm, and for example approximately 80 mm.

The guide device 2 further comprises adjustment means arranged to adjust the position of the reference member 5 with respect to the guide body 3, and so as to adjust the distance D1 between the bearing portion 12 and the axis A of the through orifice 8.

According to the embodiment shown in FIGS. 1 to 4, the adjustment means include a stop ring 16 assembled around the reference pin 11 and movable along the latter, and graduations 17 provided on the reference member 11 and representing the distance between the bearing portion 12 and the axis A of the through orifice 8. The stop ring 16 is arranged on the one hand to be positioned across from a graduation 17 representing a value of the distance D1 previously determined by the surgeon before the operation using a scan of the patient to be treated, and on the other hand to cooperate with the mounting portion 14 so as to limit the insertion travel of the reference pin 11 into the assembly orifice 15. Thus, when the stop ring 16 abuts against the mounting portion 14, the bearing portion 12 is at the desired distance D1 from the axis A of the through orifice 8.

The adjustment means may further include immobilizing means arranged to immobilize the stop ring 16 on the reference pin 11. Such immobilizing means make it possible to avoid a relative movement between the stop ring 16 and the reference pin 11 when the stop ring comes into contact with the mounting portion 14. The immobilizing means of the stop ring may for example include a pressure screw (not shown in the figures) capable of cooperating with the reference pin 11. Alternatively, the inner surface of the stop ring 16 may have a significant friction coefficient limiting unwanted relative movement between the stop ring 16 and the reference pin 11. The stop ring 16 may for example be elastically deformable.

A method for placing a glenoid implant using the guide device 2 will now be described.

Such a method comprises the following steps consisting of:
defining, using a scan of the shoulder to be treated of a patient, the optimal distance D1 as a function of the patient's anatomy,
positioning the stop ring 16 across from the graduation 17 corresponding to the previously defined distance D1,
implanting a support and guide pin 19 in the glenoidal cavity 21 of the scapula 22 to be treated substantially along the anatomical axis of the glenoid,
inserting a burr around the support pin 19 so as to form a concave spherical surface portion in the glenoidal cavity 21, said concave spherical surface portion being complementary to the bearing surface 7 of the bearing portion 6 of the guide device 2,
inserting the support pin 19 into the through orifice 8 of the bearing portion 6,
putting the bearing surface 7 of the bearing portion 6 in contact with the concave spherical surface portion previously formed in the glenoidal cavity 21,
positioning the guide device 2 in a horizontal plane, inserting the reference pin into the assembly orifice 15 of the mounting portion 14 until the stop ring 16 bears against the mounting portion 14, if necessary, angularly moving the guide device 2 with respect to the support pin 19 in the horizontal plane until bearing is obtained of the bearing portion 12 against the outer anterior cortex of the scapula 22 and of the stop ring 16 against the mounting portion 14, successively inserting a piercing tool into the through bores 9 of the bearing portion 6 so as to form bone holes in the glenoidal cavity 21, implanting the fastening elements, such as fastening studs, of the glenoid implant in the bone holes previously formed.

In the case where the glenoid implant is provided with a fastening fin instead of fastening studs, the surgeon produces a notch between the two bone holes so as to join them and implants the fastening fin in the obtained housing.

FIGS. 5 to 7 show a guide device 2 according to a second embodiment that differs from that shown in FIGS. 1 to 4 essentially in that it comprises a guide member 24 rotatably mounted with respect to the guide body 3, the guide member 24 including a passage channel 25 arranged to emerge across from the through orifice 8 and designed for passage of the support pin 19. Advantageously, the passage channel 25 has a passage cross-section that is smaller than the passage cross-section of the through orifice 8.

As shown more particularly in FIGS. 6 and 7, the guide member 24 comprises a groove 26 in the shape of an arc of circle with an axis passing through the center of the convex spherical surface portion, and the guide device 2 comprises two studs 27 mounted on the bearing portion 6 and extending parallel to the axis of the arc of circle-shaped groove 26, the studs 27 being arranged to cooperate with the arc of circle-shaped groove 26 so as to guide the rotation of the guide member 24 with respect to the bearing portion 6.

In order to ensure optimal rotational driving, the guide member 24 comprises a first guide surface 28 formed by a cylindrical surface portion with an axis combined with the axis of the groove 26 and in which the passage channel 25 emerges, and the bearing portion 6 comprises a second guide surface 29 complementary to the first guide surface 28 and in which the through orifice 8 emerges.

The guide member 24 additionally comprises fastening means arranged to fasten the guide member 24 on the support pin 19 when the latter is inserted into the through orifice 8 and extends in the passage channel 25. The fastening means advantageously include a pressure screw 31 capable of cooperating with the support pin 19. Such fastening means make it possible to keep the convex and concave spherical surface portions in contact during the insertion of the reference pin 11 into the assembly orifice 15. Furthermore, the configuration of the guide member 24 makes it possible to authorize angular travel of the guide body 3 with respect to the support pin 19, including when the latter is fastened on the guide member 24.

Figure 8:
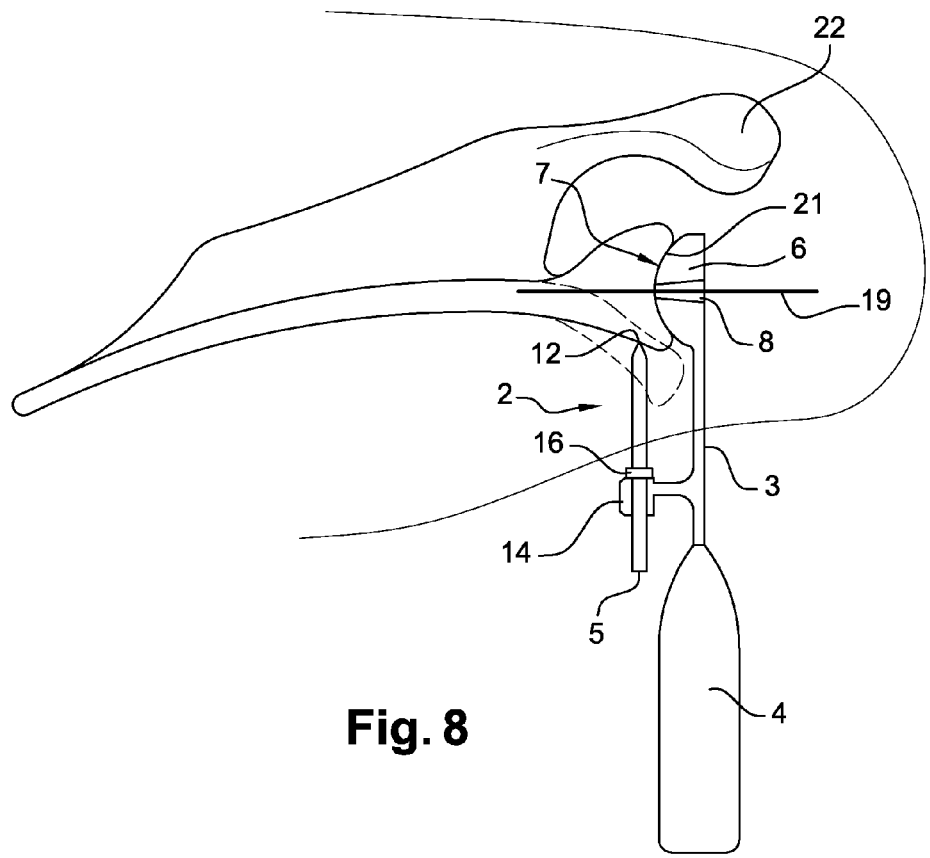
FIG. 8 is a cross-sectional view of a device for guiding piercing tools according to a third embodiment of the invention.

FIG. 8 shows a guide device 2 according to a third embodiment that differs from that shown in FIGS. 1 to 4 essentially in that the reference member 5 is formed by a rectilinear pin.

Figure 9:
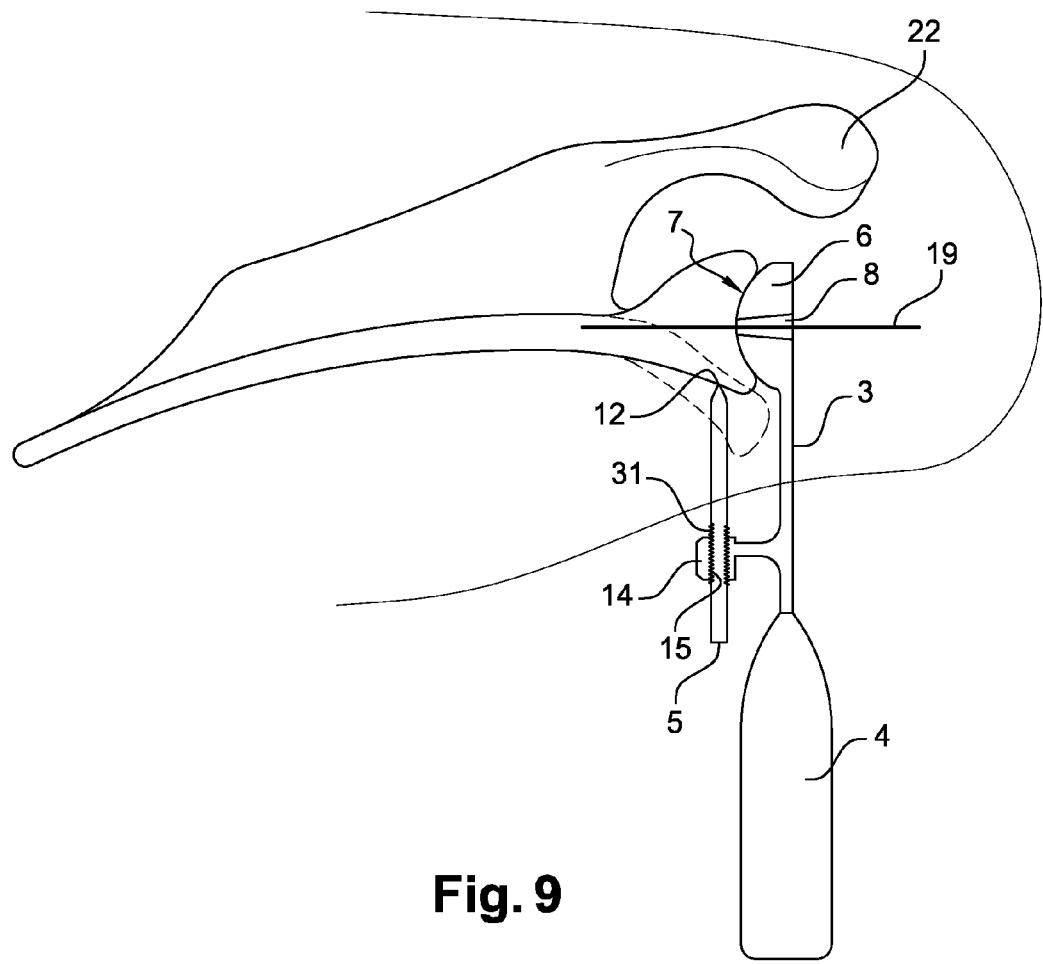
FIG. 9 is a cross-sectional view of a device for guiding piercing tools according to a fourth embodiment of the invention.

FIG. 9 shows a guide device 2 according to a fourth embodiment that differs from that shown in FIG. 7 essentially in that the adjustment means include, in place of the stop ring 16, a thread 32 formed on the reference member 5 and arranged to cooperate with a tapping formed in the assembly orifice 15 provided on the mounting portion 14.

Figure 10:
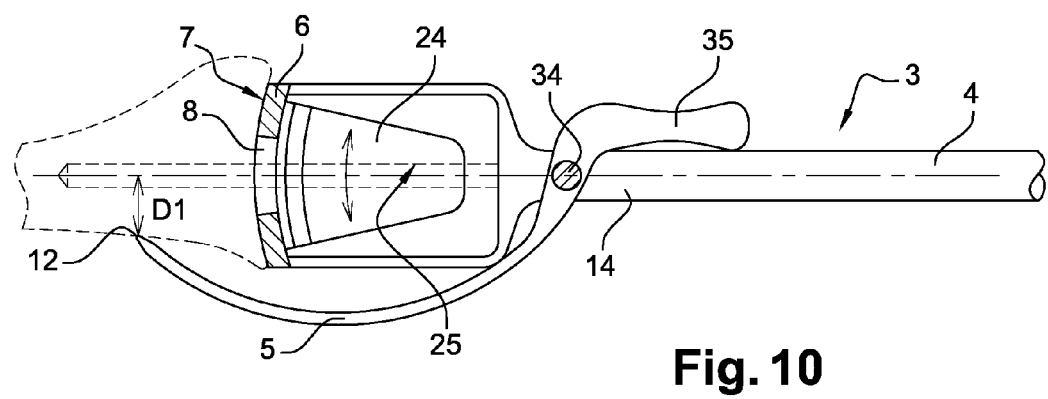
FIG. 10 is a partial top view of a device for guiding piercing tools according to a fifth embodiment of the invention.

FIG. 10 shows a guide device according to a fifth embodiment that differs from that shown in FIGS. 5 to 7 essentially in that the reference member 5 is pivotably mounted on the mounting portion 14 around a pivot axis 34 extending substantially parallel to the axis of rotation of the guide member 24, and the adjustment means including an actuating handle 35 secured to the reference member.

Advantageously, the adjustment means comprise immobilizing means arranged to immobilize the reference member 5 in a predetermined position so as to adjust the distance D1 to a desired value. Graduations representing the distance D1 may optionally be provided on the mounting portion 14 or the pivot axis 34, and a reference designed to be positioned across from the graduations may optionally be provided on the reference member 5 or the actuating handle 35.

The invention is of course not limited solely to the embodiments of the guide device described above as examples, but on the contrary encompasses all alternative embodiments.

The invention claimed is:

1. A guide device for guiding piercing tools for placing a glenoid implant, comprising:
    a guide body comprising a bearing surface designed to bear in a glenoidal cavity of a scapula that has been prepared beforehand, the guide body comprising at least one through orifice emerging in the bearing surface,
    a reference member mounted on the guide body and including a bearing portion designed to bear on the anterior cortex of the scapula,
    an adjustment assembly configured to adjust the position of the reference member with respect to the guide body so as to adjust the distance between the bearing portion and an axis of the through orifice, and
    a support pin configured to be implanted in the glenoidal cavity and inserted into the through orifice,
    wherein the height of the through orifice substantially corresponds to the diameter of the support pin,
    wherein the through orifice further includes a travel portion arranged so as to allow an angular travel of the guide body along a travel plane when the support pin is implanted in the glenoidal cavity and is inserted into the through orifice.

2. The guide device according to claim 1, wherein the guide body comprises an mounting portion on which the reference member is movably mounted.

3. The guide device according to claim 2, wherein the adjustment assembly includes a stop member movably assembled on the reference member, the stop member being arranged to cooperate with the mounting portion so as to limit the travel of the reference member with respect to said mounting portion in at least one movement direction.

4. The guide device according to claim 3, wherein the adjustment assembly includes an immobilizing component configured to immobilize the stop member with respect to the reference member.

5. The guide device according to claim 2, wherein the adjustment assembly includes a thread formed on the reference member and arranged to cooperate with a tapped assembly orifice formed on the mounting portion.

6. The guide device according to claim 2, wherein the reference member is pivotably mounted on the mounting portion around a pivot axis, and the adjustment assembly includes an actuating handle secured to the reference member.

7. The guide device according to claim 2, wherein the adjustment assembly further includes an immobilizing component configured to immobilize the reference member with respect to the guide body.

8. The guide device according to claim 1, wherein the adjustment assembly includes graduations provided on the reference member and representing the distance between the bearing portion and the axis of the through orifice.

9. The guide device according to claim 1, further comprising a guide member including a passage channel arranged to emerge across from the through orifice and designed for the passage of the support pin, the guide member being mounted rotatably with respect to the guide body around an axis of rotation.

10. The guide device according to claim 9, wherein the guide member comprises a groove in the shape of an arc of circle with an axis substantially combined with the axis of rotation, and the guide device comprises at least two studs assembled on the guide body and arranged to cooperate with the arc of circle-shaped groove.

11. The guide device according to claim 9, wherein the guide member comprises a first guide surface formed by a cylindrical surface portion with an axis substantially combined with the axis of rotation and in which the passage channel emerges, and the guide body comprises a second guide surface complementary to the first guide surface and in which the through orifice emerges.

12. The guide device according to one of claim 9, wherein the guide member comprises a fastening member configured to fasten the guide member on the support pin inserted into the through orifice and extending in the passage channel.

13. The guide device according to claim 1, wherein the bearing surface is formed by a convex spherical surface portion.

14. The guide device according to claim 1, wherein the guide body further comprises at least two through bores emerging in the bearing surface and each designed for the passage of a piercing tool.

15. A guide device for guiding piercing tools for placing a glenoid implant, comprising:
 a guide body comprising a bearing surface designed to bear in a glenoidal cavity of a scapula that has been prepared beforehand, the guide body comprising at least one through orifice emerging in the bearing surface,
 a reference member mounted on the guide body and including a bearing portion designed to bear on the anterior cortex of the scapula,
 adjustment means arranged to adjust the position of the reference member with respect to the guide body so as to adjust the distance between the bearing portion and an axis of the through orifice, and
 a support pin configured to be implanted in the glenoidal cavity and inserted into the through orifice,
 wherein the height of the through orifice substantially corresponds to the diameter of the support pin,
 wherein the through orifice further includes a travel portion arranged so as to allow an angular travel of the guide body along a travel plane when the support pin is implanted in the glenoidal cavity and is inserted into the through orifice.

16. The guide device according to claim 15, wherein the travel portion is oblong.

17. A method placing a glenoid implant, including:
 providing a guide device comprising:
  a guide body comprising a bearing surface designed to bear in a glenoidal cavity of a scapula that has been prepared beforehand, the guide body comprising at least one through orifice emerging in the bearing surface,
  a reference member mounted on the guide body and including a bearing portion designed to bear on the anterior cortex of the scapula,
  adjustment means arranged to adjust the position of the reference member with respect to the guide body so as to adjust the distance between the bearing portion and an axis of the through orifice, and
  a support pin configured to be implanted in the glenoidal cavity and inserted into the through orifice, wherein the through orifice further includes a travel portion arranged so as to allow an angular travel of the guide body along a travel plane when the support pin is inserted into the through orifice,
 adjusting the position of the reference member with respect to the guide body,
 implanting the support pin in a glenoidal cavity of a scapula to be treated,
 forming a concave spherical surface portion in the glenoidal cavity,
 inserting the support pin into the through orifice of the guide body,
 putting the bearing surface of the guide body in contact with the concave spherical surface portion formed in the glenoidal cavity,
 positioning the guide body in a horizontal plane,
 angularly moving the guide body with respect to the support pin in the horizontal plane to obtain a bearing of the bearing portion against the anterior cortex of the scapula, and
 inserting a piercing tool into the through orifice of the guide body so as to form a bone hole in the glenoidal cavity.

* * * * *